United States Patent [19]

Falcone

[11] Patent Number: 5,438,983
[45] Date of Patent: Aug. 8, 1995

[54] PATIENT ALARM DETECTION USING TREND VECTOR ANALYSIS

[75] Inventor: Ronald Falcone, Hudson, N.H.

[73] Assignee: Hewlett-Packard Company, Palo Alto, Calif.

[21] Appl. No.: 121,002

[22] Filed: Sep. 13, 1993

[51] Int. Cl.⁶ .............................................. A61B 5/00
[52] U.S. Cl. ..................... 128/630; 128/633; 128/666; 128/635; 128/672; 128/677; 128/687; 128/691; 128/716; 128/736; 128/748; 128/713; 128/668; 340/573
[58] Field of Search ................. 128/630, 632–635, 128/637, 664–673, 677–698, 700–730, 736, 748; 364/413.02–413.05; 340/573

[56] References Cited

U.S. PATENT DOCUMENTS

| | | | |
|---|---|---|---|
| 4,513,294 | 4/1985 | Anderson et al. | 128/716 |
| 4,697,450 | 10/1987 | Bachman et al. | 128/635 |
| 4,869,253 | 9/1989 | Craig, Jr. et al. | 128/665 |
| 4,944,305 | 7/1990 | Takatsu | 128/683 |
| 5,197,480 | 3/1993 | Gebhardt | 128/697 |
| 5,262,944 | 11/1993 | Weisner et al. | 364/413.02 |

FOREIGN PATENT DOCUMENTS 1502679  3/1978  United Kingdom .

OTHER PUBLICATIONS

J. H. Philip, "Thoughtful Alarms" in J. S. Gravenstein et al, eds., Essential Noninvasive Monitoring in Anesthesia, 1980, pp. 191–201.

J. H. Philip, "Overview: Creating Practical Alarms for the Future", 1989.

*Primary Examiner*—Lee S. Cohen
*Assistant Examiner*—Robert L. Nasser, Jr.

[57] ABSTRACT

A method and apparatus for detecting an alarm in a patient monitoring system. The patient monitoring system executes the steps of measuring values representative of a physiological parameter of a patient, determining whether the parameter values are within safe zone limits, initiating calculation of a trend vector that is a function of changes in the parameter values, when the parameter values go outside the safe zone limits, comparing the trend vector with an alarm limit function and issuing an alarm when the trend vector exceeds the alarm limit function. The alarm limit function typically varies with time after initiating calculation of the trend vector. The trend vector is calculated for each measured value until an alarm is issued or the parameter value returns to within the safe zone limits.

9 Claims, 5 Drawing Sheets

PATIENT ALARM DETECTION USING TREND VECTOR ANALYSIS

FIELD OF THE INVENTION

This invention relates to medical monitoring of patients and, more particularly, to improved methods and apparatus for alarm detection in patient monitoring systems.

BACKGROUND OF THE INVENTION

Patient monitoring systems are commonly used for monitoring the condition of a patient, such as in coronary care units and intensive care units of a hospital. Such systems typically include a bedside monitor having one or more sensors, such as ECG sensors, blood pressure sensors and temperature sensors, attached to the patient. The sensors measure various physiological parameters of the patient. The measured parameters are processed by a system processor and may be displayed on a video display screen and stored for later analysis. Patient physiological information from several bedside monitors may be forwarded to a central station located, for example, at a nursing station.

The bedside patient monitor and the central station may display physiological parameters as waveforms and/or numerical values. Another important function of patient monitoring systems is to generate alarms when one or more of the physiological parameters indicates that the patient requires attention. Such alarms are necessary because it is not feasible for the display screen of the patient monitoring system to be observed continuously. Alarms are typically annunciated both visibly and audibly.

The conventional way of specifying alarm criteria, shown in FIG. 5, is to set an upper threshold 102 and a lower threshold 104 for a measurement, such as heart rate. When the measured value goes above the upper threshold 102 or below the lower threshold 104, an alarm is issued. The thresholds are fixed as a function of time, except for exclusionary zones 106 and 108 which permit brief excursions outside the thresholds without issuing an alarm. It may be difficult to select thresholds which produce clinically acceptable results, while avoiding excessive false alarms. When the threshold is close to the desired value, false alarms may occur frequently; and when the threshold is spaced from the desired value, clinically significant alarm conditions may not be detected. In some cases, users of the patient monitoring system may wish to have the monitoring system generate an alarm when there is a sudden but significant change in the patient's condition or when there is a slow, gradual deterioration in the patient's condition. The conventional fixed thresholds do not adequately detect these conditions. Others have combined such thresholds with other techniques, such as fixed delays, hysteresis, or refractory periods. A problem with processes that use combinations of these techniques is that as additional constraints are applied to the process, the process complexity rises dramatically, and quickly reaches a point where implementing new functionality is not economically feasible; thus, it is desirable to be able to describe complex timing conditions and thresholds in a single process. Various, more sophisticated alarm criteria have been proposed. See, for example, J. H. Philip, "Thoughtful Alarms", in J. S. Gravenstein et al, eds. *Essential Noninvasive Monitoring in Anesthesia,* 1980, page 191-201, and J. H. Philip, "Overview: Creating Practical Alarms for the Future", 1989. Such systems may be unnecessarily complex for relatively straightforward patient monitoring requirements.

SUMMARY OF THE INVENTION

According to a first aspect of the invention, a method for detecting a patient alarm is provided. The method is used in a patient monitoring system that includes at least one sensor for measuring values representative of a physiological parameter and a processor for processing the measured values and for providing information representative of the parameter values. In the method for detecting an alarm in accordance with the invention, the patient monitoring system executes steps comprising measuring values representative of a physiological parameter, determining whether the parameter values are within safe zone limits, initiating calculation of a trend vector that is a function of changes in the parameter values and time, when the parameter values go outside the safe zone limits, comparing the trend vector with an alarm limit function and issuing an alarm when the trend vector exceeds the alarm limit function.

The alarm limit function preferably comprises a change limit that varies with time after initiating calculation of the trend vector. Different alarm limit functions may be used for positive and negative trend vectors. An alarm can be issued only when the trend vector is outside a predefined exclusionary zone which typically defines changes that are too short to be of interest or which are physiologically impossible. The trend vector is calculated for each new parameter value outside the safe zone limits. Calculation of the trend vector is discontinued when the parameter values return to within the safe zone limits.

According to another aspect of the invention, a patient monitoring system comprises a sensor for measuring values representative of a physiological parameter and a processor for processing the parameter values. The processor comprises means for determining whether the parameter values are within safe zone limits, means for initiating calculation of a trend vector when the parameter values go outside the safe zone limits, means for comparing the trend vector with an alarm limit function and means for issuing an alarm when the trend vector exceeds the alarm limit function.

The patient monitoring system preferably includes a display unit. In this case, the processor includes means for displaying information representative of the measured values of the physiological parameter on the display unit. The processor can include means for displaying the trend vector on the display unit as an arrow having a direction that indicates a polarity of change in the parameter values and having a length that indicates a magnitude of change in the parameter values. Optionally, the trend arrow may indicate magnitude with color, or color can be used to indicate the alarm state of the parameter.

According to a further aspect of the invention, a method for displaying information representative of a physiological parameter is provided. The method is used in a patient monitoring system that includes at least one sensor for measuring values representative of the physiological parameter, a processor for processing the measured values and a display unit. The patient monitoring system executes steps comprising measuring values representative of the physiological parameter, determining a trend in the parameter values over a specified time period, and displaying an indication of the trend on the display unit.

BRIEF DESCRIPTION OF THE DRAWINGS

For a better understanding of the present invention, reference is made to the accompanying drawings, which are incorporated herein by reference and in which.

DETAILED DESCRIPTION

Figure 1:
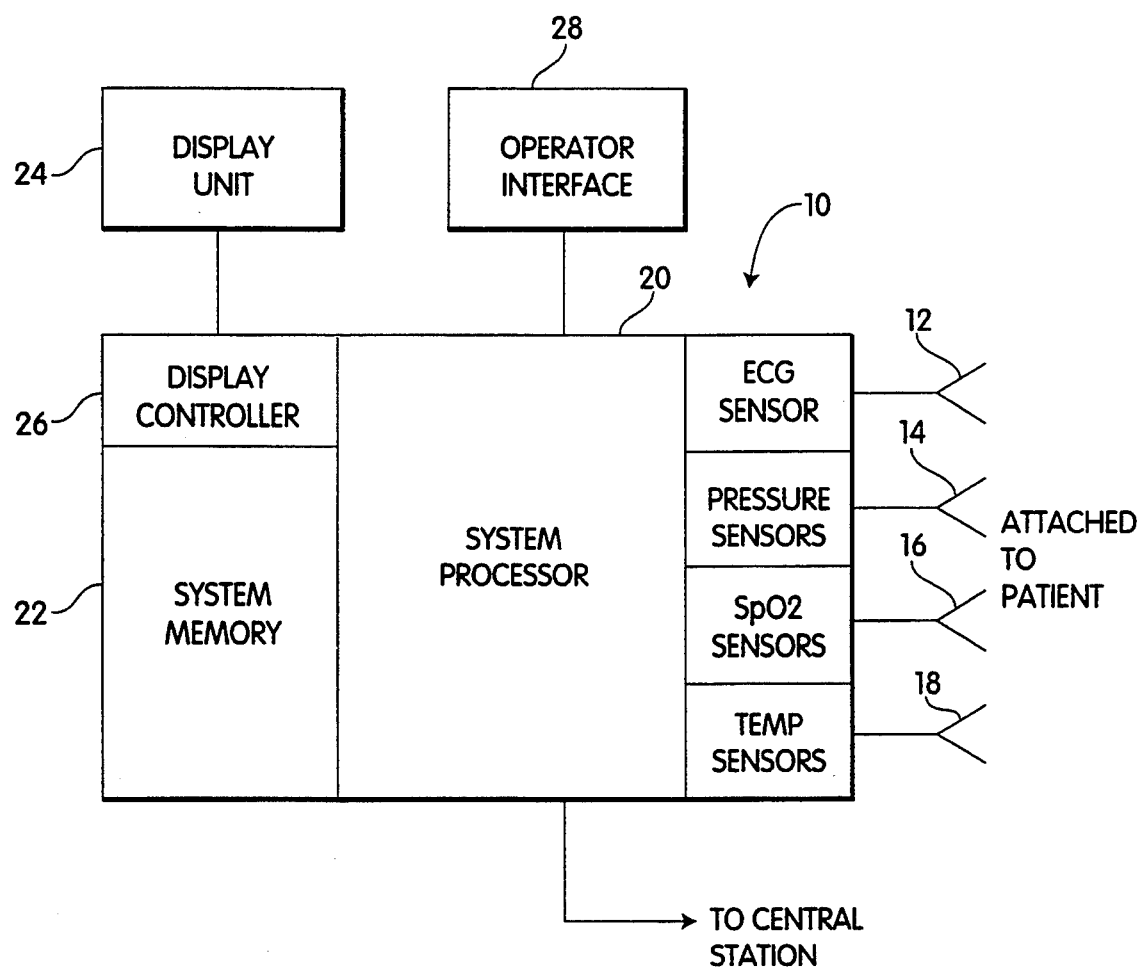
FIG. 1 is a block diagram of a patient monitoring system suitable for incorporation of the present invention.

A block diagram of a patient monitoring system suitable for incorporation of the alarm detection technique of the present invention is shown in FIG. 1. A bedside monitor 10 is typically located at a patient's bedside and includes one or more transducers, or sensors, attached to the patient. The transducers may include ECG sensors 12, pressure sensors 14, SpO$_2$ sensors 16 and temperature sensors 18. The number and type of sensors is optional. The sensors sense various physiological parameters of interest.

The physiological parameter measurements obtained by the sensors are supplied to a system processor 20. Typically, analog sensor output signals are amplified and are converted to digital data by an analog-to-digital converter (not shown). The digital data representing the sensor signals is supplied to the system processor 20. The system processor 20 operates in conjunction with a system memory 22, a display unit 24, typically a video display screen, a display controller 26 and an operator interface 28 to monitor the patient's condition and to supply information to a user. The system processor 20 may, for example, include a Motorola 680X0 microprocessor.

The information presented on the display unit 24 may include waveforms of one or more physiological parameters, numerical values of one or more physiological parameters and alarm conditions which indicate that the patient requires attention. The physiological parameter information obtained by the sensors can be stored in a system memory 22 for subsequent analysis. Information regarding the patient's condition can also be supplied to a central station. An example of a bedside monitor of the type shown in FIG. 1 is the Model M1176A, manufactured and sold by Hewlett-Packard Company.

Figure 2:
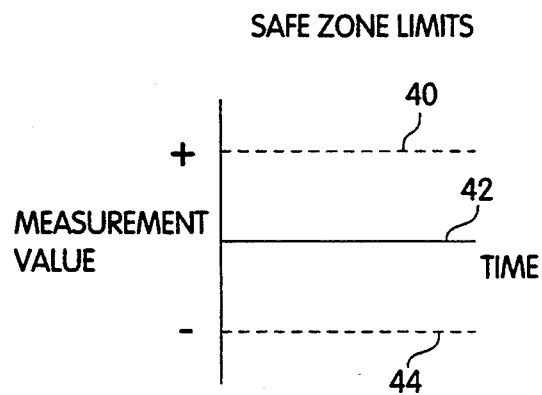
FIG. 2 is a graph of measurement value as a function of time, indicating safe zone limits utilized in accordance with the present invention.

A technique for alarm detection, called the vector intercept method, in accordance with the present invention is illustrated with reference to FIGS. 2 and 3. As shown in FIG. 2, safe zone limits are established for each physiological parameter. The physiological parameter can be a directly measured parameter or one that is calculated from one or more measured values. Examples of calculated parameters include heart rate and cardiac index. The safe zone limits are defined by an upper limit 40 above a nominal parameter value 42 and a lower limit 44 below the nominal parameter value 42. As will become apparent, the safe zone limits 40 and 44 can, when appropriate, be closer to the nominal parameter value 42 than the thresholds used in conventional alarm techniques without significantly increasing the false alarm rate. When a measured value is between the safe zone limits 40 and 42, no alarm can be generated. When the measured value goes above the upper limit 40 or below the lower limit 44, a trend vector analysis is initiated as described below.

Figure 3:
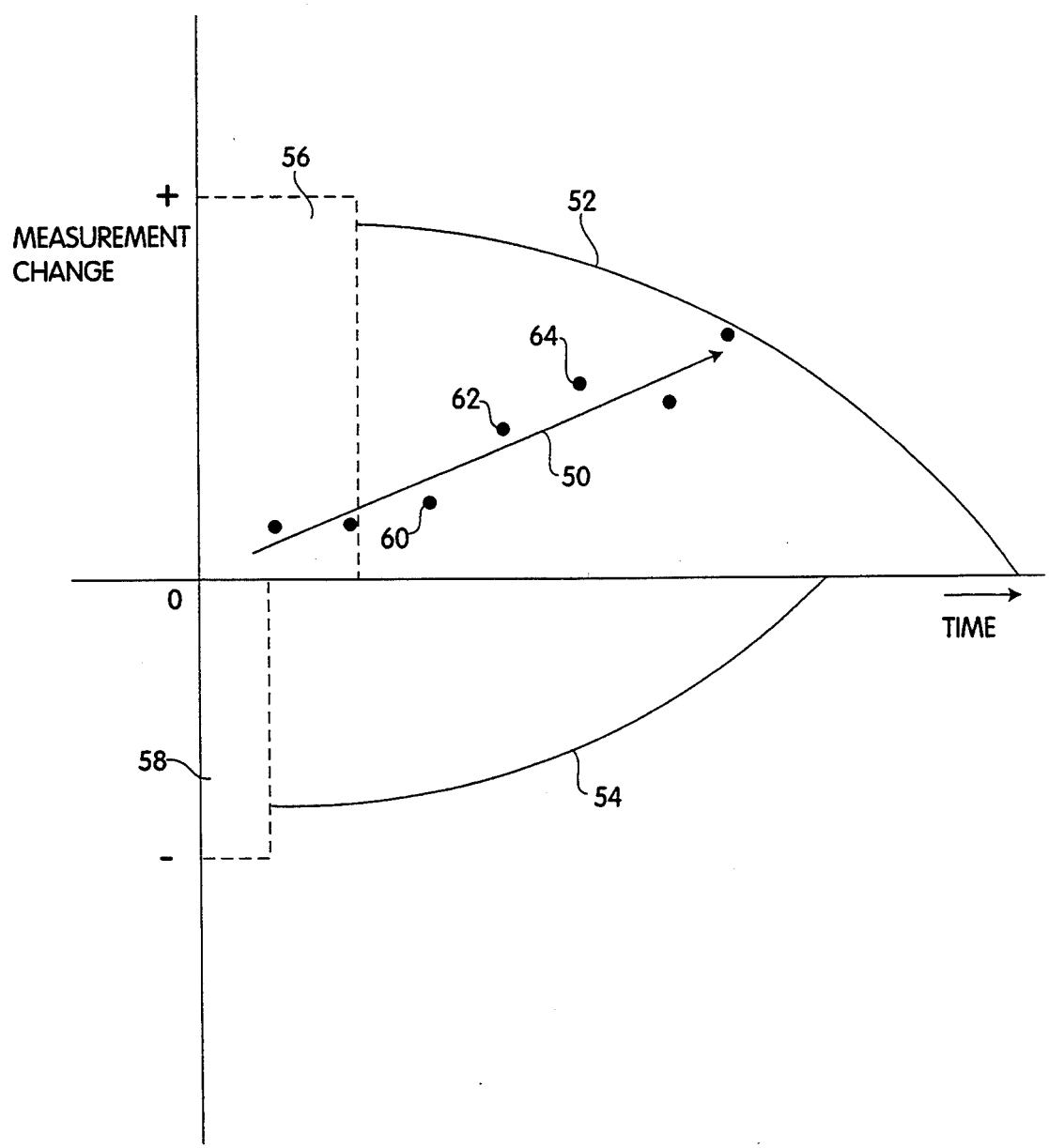
FIG. 3 is a graph of measurement change as a function of time, illustrating the trend vector utilized in the present invention.

When the measured value of the physiological parameter goes outside the safe zone limits of the physiological parameter, a trend vector analysis is initiated as shown in FIG. 3. A trend vector 50 depends on a measurement change since initiation of the trend vector analysis and the time since initiation of the trend vector analysis. Both a magnitude and a polarity are associated with the measurement change. Typically, measurement values are obtained at periodic intervals, such as one second intervals. After initiation of the trend vector analysis, a trend vector is preferably calculated for each measured value of the physiological parameter until the trend vector analysis is terminated as described below. By way of example, if the heart rate changes from 80 to 90 in a period of 20 seconds, the trend vector can be represented by a measurement change of 10 in a time of 20 seconds.

The trend vector 50 is an approximation to the values of measurement change of the physiological parameter. Measured values continue to be obtained at periodic intervals after the parameter values go outside the safe zone limits (at time zero). From the measured values, values of measurement change relative to the measured value at the time when the parameter went outside the safe zone limits are determined. The values of measurement change are illustrated as points 60, 62, 64, etc. in FIG. 3. The trend vector 50 is preferably a straight line approximation to the values of measurement change. In a preferred embodiment, a conventional least squares approximation is used to calculate the trend vector 50. The trend 50 is calculated for each new measured value.

Each calculated trend vector 50 is compared with an alarm limit function 52 or 54. The alarm limit functions 52 and 54 typically vary with time, starting when the trend vector analysis is initiated. In one embodiment, the alarm limit functions are straight lines that connect the maximum allowable change in the shortest interval and the minimum allowable change in the longest interval. Alternatively, the alarm limit functions 52 and 54 can be established by plotting clinically significant changes as a function of time. In general, the alarm limit functions 52 and 54 can be arbitrary functions of time. The alarm limit functions for positive and negative measurement changes can be the same or different. As long as the trend vector 50 does not exceed the appropriate alarm limit function, no alarm is generated, and monitoring of the measurement values continues. When the trend vector 50 exceeds one of the alarm limit functions, an alarm is generated. It will be understood that the alarm limit function may have a different value for each time interval after initiation of the trend vector analysis. Thus, for example, the alarm limit may be reduced as time progresses.

The trend vector analysis may optionally include exclusionary zones 56 and 58. When the trend vector 50 falls within one of the exclusionary zones 56 or 58, no alarm can be generated. The exclusionary zones 56 and 58 represent changes which are too short to be of interest, which are physiologically impossible or for which an alarm is otherwise not desired. For example, there is no way that the blood pressure can double in less than three seconds, so a blood pressure alarm in this condition would not be appropriate. The exclusionary zones 56 and 58 can be defined arbitrarily and can be different for positive and negative measurement changes.

The trend vector analysis continues until it is terminated. Termination can occur in one of two ways. When an alarm is issued, as described above, the trend vector analysis is terminated. Also, if the measured value of the physiological parameter returns to within the safe zone limits as shown in FIG. 2, the trend vector analysis is terminated and the measurement parameter values are monitored normally to determine whether they are within the safe zone limits.

Figure 4A:
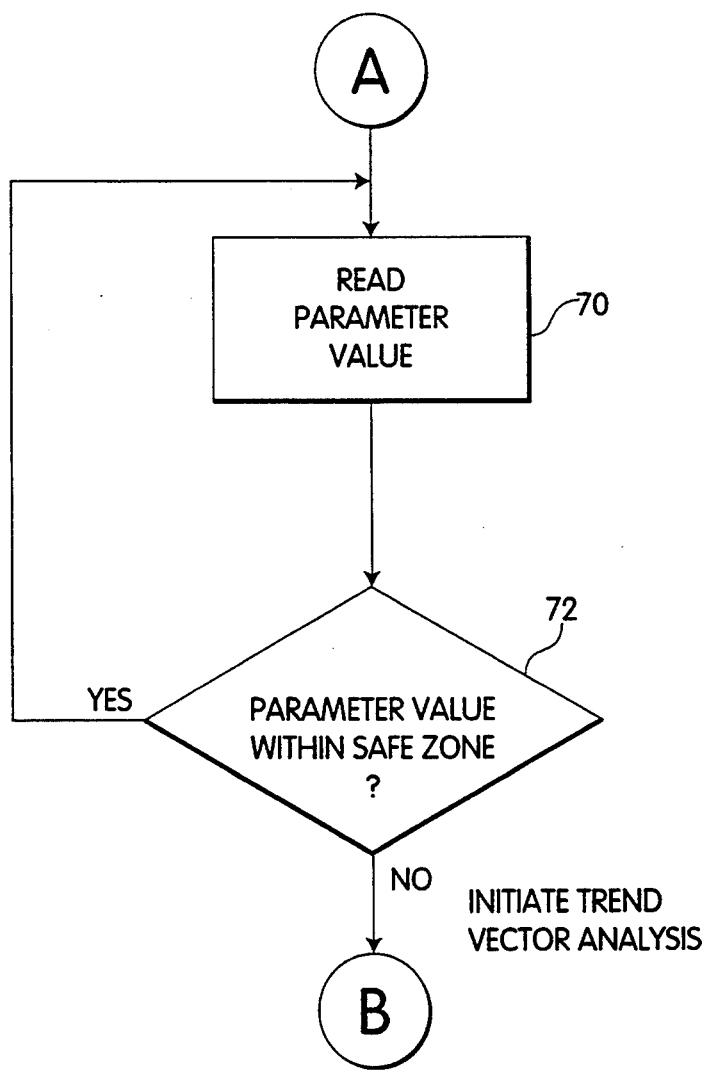
FIGS. 4A and 4B show a flow diagram of the method for detecting an alarm in accordance with the present invention.
Figure 4B:
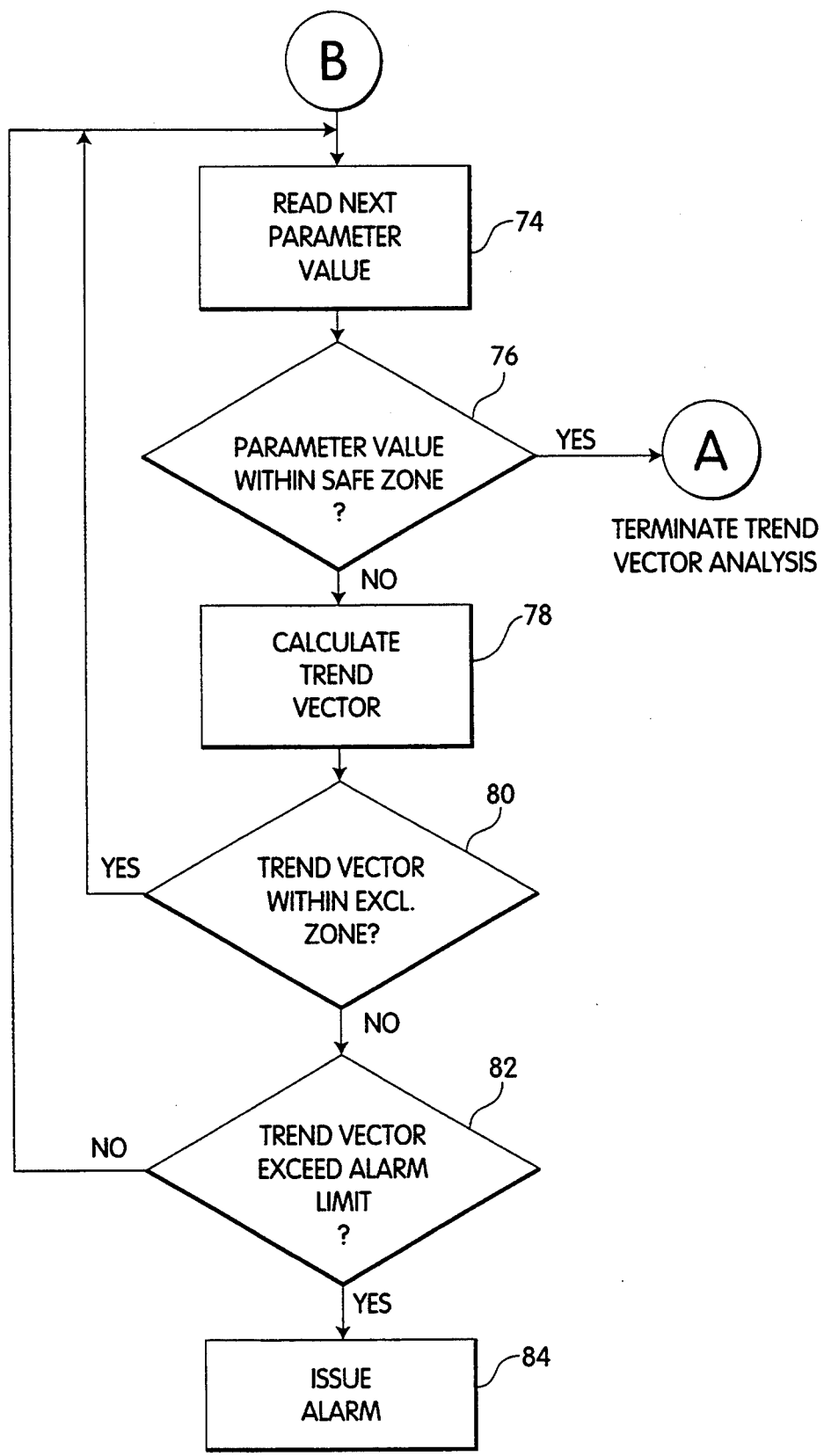
Figure 5:
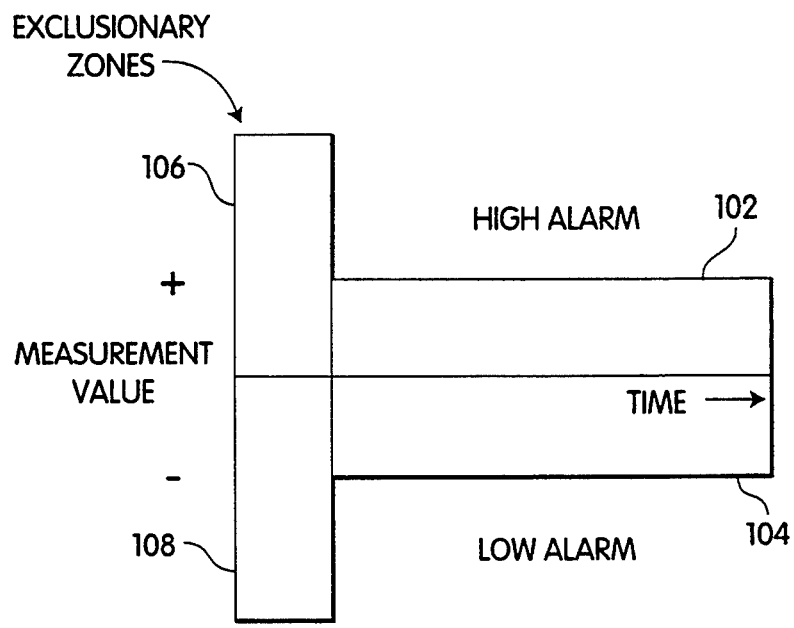
FIG. 5 is a graph of measurement value as a function of time, indicating alarm limits used in the prior art.

A flow diagram of the alarm detection technique of the present invention is shown in FIGS. 4A and 4B. In a preferred embodiment, the alarm detection technique of the invention is implemented as a software program which is executed on system processor 20 (FIG. 1). The invention can, for example, be implemented in the C/C++ programming language.

A parameter value is read by system processor 20 in step 70. As stated above, the output of each sensor is converted to digital data at periodic intervals, and the digital data is supplied to system processor 20. The parameter value is compared with the upper limit 40 and the lower limit 44 of the safe zone to determine whether the parameter value is within the safe zone limits in step 72. When the parameter value is within the safe zone limit, no action is required and the process returns to step 70 to read the next parameter value.

When the parameter value is outside the safe zone, trend vector analysis is initiated as shown in FIG. 4B. The next parameter value is read in step 74. The new parameter value is compared with the safe zone limits 40 and 44 in step 76. When the new parameter value is outside the safe zone limits, a trend vector is calculated in step 78. As stated above, a least squares fit calculation can be utilized. The trend vector is then compared with an exclusionary zone in step 80. When the trend vector is within the exclusionary zone, no action is required, and the process returns to step 74 to read the next parameter value. It will be understood that the exclusionary zone is optional and may not be utilized in some applications. When the trend vector is outside the exclusionary zone, it is compared with the appropriate alarm limit function in step 82. As stated above, the alarm limit function typically varies with time. When the trend vector does not exceed the alarm limit function for that time, no action is required, and the process returns to step 74 to read the next parameter value. When the trend vector does exceed the alarm limit function, an alarm is issued in step 84. The trend vector analysis is then terminated.

Referring again to step 76, when any of the measured parameter values falls within the safe zone limits, the trend vector analysis is terminated, and the process returns to step 70 (FIG. 4A) for normal comparison of the measured parameter value with the safe zone limits 40 and 44.

The trend vector can be displayed on the display unit 24 as an arrow having a direction that indicates a polarity of change in the measured parameter values and having a length that indicates a magnitude of change in the measured parameter values. Optionally, the trend arrow may indicate magnitude with color, or color can be used to indicate the alarm state of the parameter.

Figure 6:
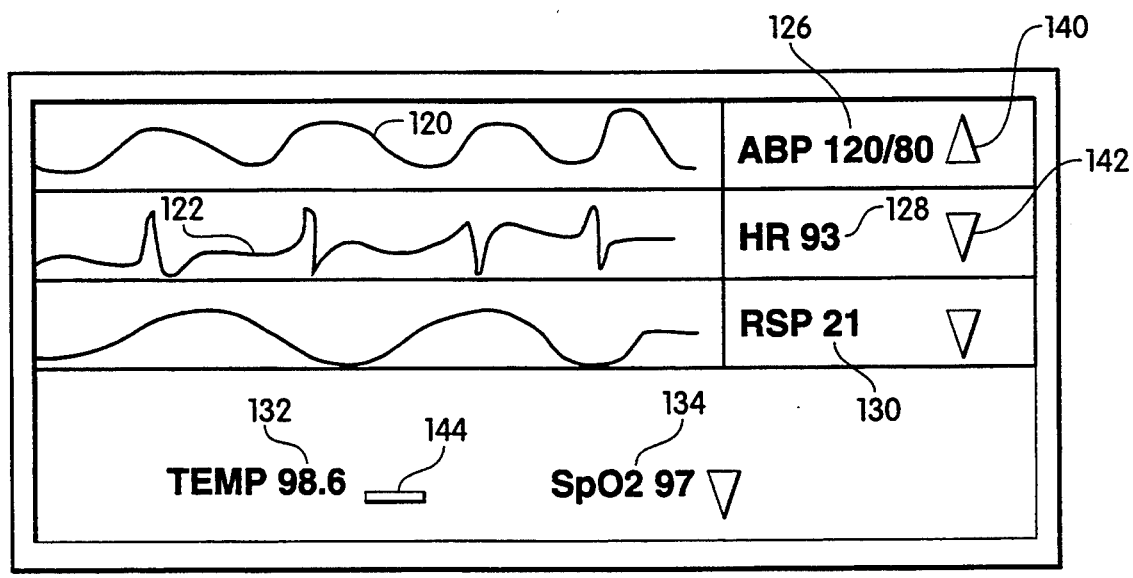
FIG. 6 is an example of a patient monitor display that indicates trends in physiological parameters.

An example of a patient monitor display containing trend vectors is shown in FIG. 6. The display can include any required information, such as waveforms 120 and 122 and current parameter values 126, 128, 130, 132 and 134. Associated with one or more current parameter values is an indication of a trend in that parameter value. In the example of FIG. 6, the trend is indicated by an up arrow 140 when the parameter is increasing or a down arrow 142 when the parameter is decreasing. A constant value can be indicated by a bar 144. Alternatively, the trend can be indicated by words such as "up" or "down", or any other desired trend indication. As noted above, the length and/or color of trend indicators, such as arrows 140 and 142, can be used to display other aspects of the trend, including magnitude and alarm state. In one embodiment, a trend indicator is displayed only when the parameter value exceeds the safe zone limits as described above. In another embodiment, a trend indicator can be displayed at all times. The utility of the trend indicators is that the clinician can look at the monitor and know not just what the current parameter values are but what the parameter values have been doing over a specified time, such as the past fifteen minutes.

Examples will now be given to illustrate the utility of the alarm detection technique of the present invention. In a first example, as a patient weakens, his or her respiration rate may very gradually deteriorate. It may take an hour or more for a conventional prior art low respiration rate alarm limit to be exceeded. By this time, the patient may be beyond help. The alarm limit may have been totally reasonable in most cases, but not in this case. The alarm detection technique described above permits this condition to be detected by reducing the threshold as the trend develops and issuing an alarm earlier, in time for intervention to provide a favorable outcome. If the alarm limits had been set initially to the level at which the alarm was issued, there would have been many false alarms.

In a second example, a patient under anesthesia may have a systolic pressure that is low, but of no real concern. After some time, reaction to a drug may cause the patient's pressure to rise rapidly. This is tolerable temporarily but if allowed to persist for the several minutes it would take to reach the prior art systolic pressure alarm limit, the patient could be severely injured. In accordance with the disclosed alarm detection technique, this situation is detected by reducing the threshold and adjusting the trend vector as the pressure continues to rise, resulting in a quicker alarm.

In a third example, a heart rate measurement of zero may indicate that a patient has gone into ventricular fibrillation or may be a consequence of a transient motion artifact. In accordance with the disclosed alarm detection technique, a trend vector would initially be computed in the exclusionary zone, and no alarm would be issued. In the case of a real emergency, subsequent values of the trend vector would exceed the alarm limit function and generate an asystole alarm in time for intervention to occur.

While there have been shown and described what are at the present considered the preferred embodiments of the present invention, it will be obvious to those skilled in the art that various changes and modifications may be made therein without departing from the scope of the invention as defined by the appended claims.

What is claimed is:

1. A patient monitoring system comprising:
    a sensor for measuring values representative of a physiological parameter; and
    a processor coupled to said sensor for processing said parameter values measured by said sensor, said processor comprising:
    means for determining whether said parameter values are within safe zone limits;
    means for initiating calculation of a trend vector when said parameter values go outside said safe zone limits, said trend vector being a function of changes in said parameter values and time;
    means for comparing said trend vector with an alarm limit function; and
    means for issuing an alarm when said trend vector exceeds said alarm limit function.

2. A patient monitoring system as defined in claim 1 wherein said processor further includes means for discontinuing calculation of said trend vector when said parameter values go within said safe zone limits.

3. A patient monitoring system as defined in claim 1 wherein said means for comparing includes means for comparing positive and negative trend vectors with different alarm limit functions.

4. A patient monitoring system as defined in claim 1 wherein said means for comparing includes means for comparing said trend vector with a limit that varies with time after initiating calculation of said trend vector.

5. A patient monitoring system as defined in claim 1 wherein said means for issuing an alarm includes means for issuing an alarm only when said trend vector is outside a predefined exclusionary zone.

6. A patient monitoring system as defined in claim 1 further including a display unit, said processor further including means for displaying information representative of the values of said physiological parameter on said display unit.

7. A patient monitoring system as defined in claim 6 wherein said processor further includes means for displaying said trend vector on said display unit as an arrow having a direction that indicates a polarity of change in said parameter values and having a length that indicates a magnitude of change in said parameter values.

8. A patient monitoring system as defined in claim 6 wherein said processor further includes means for displaying said trend vector on said display unit as an arrow having a direction that indicates a polarity of change in said parameter values and having a color that indicates a magnitude of change in said parameter values.

9. A patient monitoring system as defined in claim 6 wherein said processor further includes means for displaying said trend vector on said display unit as an arrow having a direction that indicates a polarity of change in said parameter values and having a color that indicates an alarm state of said physiological parameter.

* * * * *